(12) United States Patent
Ljunström et al.

(10) Patent No.: US 8,088,075 B2
(45) Date of Patent: Jan. 3, 2012

(54) IDENTIFICATION OF AN IMPLANTABLE MEDICAL DEVICE BY CORRELATING CARDIAC RELATED DATA

(75) Inventors: Jan Ljunström, Hässelby (SE); Hans Abrahamson, Stockholm (SE); Leif Lindkvist, Stenhamra (SE); Stefan Wahlberg, Stockholm (SE); Niklas Sköldengen, Täby (SE)

(73) Assignee: St. Jude Medical AB, Jarfalla (SE)

( * ) Notice: Subject to any disclaimer, the term of this patent is extended or adjusted under 35 U.S.C. 154(b) by 334 days.

(21) Appl. No.: 12/514,148

(22) PCT Filed: Nov. 30, 2006

(86) PCT No.: PCT/SE2006/001377
§ 371 (c)(1),
(2), (4) Date: May 8, 2009

(87) PCT Pub. No.: WO2008/066425
PCT Pub. Date: Jun. 5, 2008

(65) Prior Publication Data
US 2010/0049272 A1 Feb. 25, 2010

(51) Int. Cl.
*A61B 5/04* (2006.01)
*A61B 5/02* (2006.01)
(52) U.S. Cl. .................. 600/508; 600/374; 600/481
(58) Field of Classification Search .............. 600/374, 600/481, 508
See application file for complete search history.

(56) References Cited

U.S. PATENT DOCUMENTS

| 4,596,255 | A | 6/1986 | Snell et al. |
| 4,791,936 | A | 12/1988 | Snell et al. |
| 5,792,205 | A | 8/1998 | Alt et al. |
| 5,974,341 | A * | 10/1999 | Er et al. ................. 607/31 |
| 6,482,154 | B1 | 11/2002 | Haubrich et al. |
| 7,850,642 | B2 * | 12/2010 | Moll et al. .............. 604/95.04 |
| 7,963,925 | B1 * | 6/2011 | Schecter ................. 600/508 |
| 2004/2115089 | | 10/2004 | Bergelson et al. |
| 2005/0070968 | A1 | 3/2005 | Bergelson et al. |
| 2006/0224213 | A1 | 10/2006 | Fuller et al. |

OTHER PUBLICATIONS

"Utility of the Surface ECG before VDD Pacemaker Implantation," Burri et al., International Journal of Cardiology, vol. 117 (2007) pp. 211-213.

* cited by examiner

*Primary Examiner* — Carl H Layno
*Assistant Examiner* — Natasha Patel
(74) *Attorney, Agent, or Firm* — Schiff Hardin LLP

(57) ABSTRACT

In a method and system for identifying an implantable medical device (IMD), which is arranged to be disposed in a body, by conducting a telemetry communication session between the implantable medical device and an external programmer device, cardiac data are registered from a point on the body of a patient having an IMD with which a communication session is to be established. The registered cardiac data are compared with one or more sets of intracardiac data pertaining to patients having an IMD implanted and to identify the IMD with which the communication session is to be conducted by the performed comparison.

13 Claims, 3 Drawing Sheets

IDENTIFICATION OF AN IMPLANTABLE MEDICAL DEVICE BY CORRELATING CARDIAC RELATED DATA

FIELD OF THE INVENTION

The present invention relates to a method and system of identifying an implantable medical device, which is arranged to be disposed in a body, for conducting a telemetry communication session between the implantable medical device and an external programmer device.

DESCRIPTION OF THE PRIOR ART

When communicating with a medical implantable device (IMD), such as a pacemaker, an insulin pump, a cardioverter defibrillator, a cardiac monitor, etc. implanted in tissue of a human or animal body, a radio frequency (RF) transceiver is used for wireless communication of signals to/from RF communication circuitry comprised in the IMD. Communication may be established with the IMD for a number of reasons. For instance, medical personnel may want to monitor and/or adjust parameters of the IMD, it may be desirable to perform medical or therapeutic treatment of the body via the IMD, e.g. defibrillation, restart of a stopped heart, injection of an insulin dose, etc. Needless to say, RF signaling enables establishment of a communication channel without having to open up the patient surgically. Hence, an RF device referred to as a programmer is employed to establish RF communication with transceiver circuitry within an IMD. From a user's point of view, a programmer may be viewed upon as a computer arranged with an RF transceiver, a user interface for controlling the programmer and a dedicated software designed for the purpose of communicating with an IMD. When establishing communication with an IMD, the programmer broadcasts a wake-up signal to which the IMD responds before a communication session may be undertaken between the programmer and the IMD, i.e. before payload data is exchanged between the programmer and the IMD.

In certain environments, such as in hospitals or other care institutions, a situation may arise where a plurality of patients carrying IMDs are located within the coverage area of a programmer. When an operator uses the programmer to broadcast an RF wake-up signal for establishing communication with an IMD, it may happen that more than one IMD responds to the broadcast. This multi-device response to a broadcast may be problematic. When receiving the response signals, the operator of the programmer does not know to which patient's IMD a given response signal corresponds. Hence, if the programmer establishes a communication session with a selected IMD responding to the broadcast signal, there is still uncertainty as to which patient's IMD the programmer communicates with.

U.S. Pat. No. 6,482,154 discloses an IMD telemetry system in which an external programmer issues a request for communication, which may be received by any of a plurality of IMDs located within communication range of the programmer. The IMDs may in response each transmit a signal indicating that the request for communication has been received. This signal includes an identifier unique to the IMD in question. Then, a response-provoking event is performed in the vicinity of an IMD implanted in a specified patient with which communication is to be undertaken, in order to cause the provoked IMD to transmit an event signal comprising the unique IMD identifier to the programmer. The response-provoking event is performed by a physician, other individual operating the programmer, or the patient herself. The IMD may be provided with an appropriate sensor capable of responding to stimuli or signals applied to the patient's body to trigger uplink transmission of an event signal. For example, a magnet may be placed adjacent to the specified IMD, triggering uplink transmission of an event signal responsive to the magnet placement. Alternatively, the patient's skin over the IMD may be tapped to create a signal detectable by a pressure or activity sensor which triggers transmission of the event signal.

The event signal is then displayed at the external programmer and/or may be indicated audibly or visibly. The operator of the external programmer either directly observes the response-provoking event when the patient is in sight, or assists the patient in timing the response-provoking event when the patient is not in sight but is at least in voice communication with the operator. If the operator observes an event signal that is transmitted by uplink telemetry from the IMD contemporaneously with a response-provoking event performed adjacent the IMD of the specified patient, it can be concluded that the IMD which transmitted the event signal is the IMD with which communication is desired and the unique identifier comprised in the event signal can be used to initiate a telemetry session with the specified IMD.

Even though the system set disclosed in U.S. Pat. No. 6,482,154 aims at assuring that communication is occurring with an IMD in a desired patient and not with some other IMD in another patient within the telemetry range by means of correlating a received uplink event signal to a response-provoking event, a problem still remains in that the operator of the external programmer is required to either directly observe the response-provoking event when the patient is in sight, or assist the patient in timing the response-provoking event when the patient is not in sight but is at least in voice communication with the operator.

SUMMARY OF THE INVENTION

An object of the present invention is to mitigate the problems set forth in the above with respect to prior art, and to provide a manner of identifying a particular patient's IMD without necessarily having to keep the patient in sight or to be within voice communication distance of the patient.

The above object is achieved in accordance with the present invention by a method and a system for identifying an implantable medical device, which is configured to be disposed in the body of a patient, by conducting a telemetry communication session between the implantable medical device and an external programmer device, wherein cardiac data are registered from a point on the body of the patient in whom the medical device is implanted, and with which a communication session is to be established. The registered cardiac data are compared with one or more sets of intracardiac data pertaining to different patients each having an implanted cardiac device, and the result of the comparison is used to identify the implanted cardiac device with which the communication session is to be conducted.

A basis of the invention is to register cardiac data from a point on the body, which data in the following is referred to as external cardiac data, of a patient having an IMD with which a communication session is to be established, compare the external cardiac data with one or more sets of intracardiac data pertaining to patients having an IMD implanted and to identify the IMD with which the communication session is to be conducted by means of the performed comparison. To this end, an operator of an external programmer device wirelessly transmits a communication-initiating signal from the programmer device. IMDs located within communication range of the programmer respond to the communication-initiating signal by transmitting intracardiac data derived from the patient in which a particular IMD is implanted and an IMD identifier. The patient with which communication is to be established is selected, and external cardiac data is registered by using appropriate measurement equipment. The registered external cardiac data is transmitted from the patient to the programmer either via wire or via the air interface. The external cardiac data is then compared to the previously received sets of intracardiac data. Note that the actual data format of the intracardiac data may be quite different from the data format of the external cardiac data, and an encoding of the intracardiac data and/or the external cardiac data may be undertaken at the programmer such that a true comparison can be made. If the external cardiac data corresponds to any one of the received intracardiac data sets, the IMD identifier associated with the matching intracardiac data set is employed to identify the IMD of the patient with which communication is to be conducted. The programmer may then use this identification to designate, and thus establish a communication session, with the desired IMD.

The present invention is advantageous for a number of reasons. First of all, when receiving a number a respective response signal from a programmer at a plurality of IMDs in reply to a wireless broadcast communication-initiating signal, it is possible to identify an IMD with which a communication is to be established from these response signals and a supplementary external cardiac data measurement. Hence, it is assured that communication is occurring with an IMD in a desired patient and not with some other IMD in another patient within the communication range of the programmer. Further, in the present invention, it is not necessary to keep the patient in sight or to be within voice communication distance of the patient. Clearly, the operator of the programmer can identify a desired IMD without having to actually see or be in voice contact with the patient.

The data obtained from one or more points on the body of a patient, i.e. the external cardiac data, may be obtained in a number of different manners. For instance, an electrocardiogram (ECG) may be registered for a patient, an oximeter can be attached to the patient's finger or ear lobe to measure oxygen pressure in the blood of the patient or the patient' pulse. Further, it is possible to measure cardiac impedance of a patient by means of attaching probes to the patient's body.

Accordingly, the intracardiac data derived from a patient in which an IMD is implanted may be attained in a number of different manners. For instance, the IMD can register an intracardiac electrogram (IEGM) or it can measure pressure in different locations in the heart, e.g. in the left ventricle, wherein a pressure curve can be obtained. Moreover, the intracardiac impedance may be measured. Typically, an IMD such as e.g. a pacemaker comprises a conductive housing and one or more pacemaker leads. The intracardiac impedance can thus be measured between the leads and the housing. A representation of the intracardiac data is compared to a corresponding representation of the external cardiac data such that a check for correspondence between the intracardiac data and the external cardiac data can be made.

In an embodiment of the present invention, a comparison for correspondence between a surface electrocardiogram data and an intracardiac electrogram is based on PQRST cycles of the respective electrogram data. Identification of a patient can be done by analyzing characteristics of typical cycles, i.e. PQRST cycles forming the ECG. These signals appear to vary from person to person according to different factors such as anatomic differences in the heart, gender, relative body weight, chest configuration, etc. Typically, relative location and amplitudes of P, Q, R, S and T peaks of the PQRST cycle is taken into consideration. In particular, R-R intervals are used as a means for comparison. Typically, the R-peaks are taken as reference because they can be more precisely and unambiguously determined as they constitute the highest peaks in the ECG signal. Further, the elements of a PQRST-cycle are contained within an R-R internal. However, it should be noted that those skilled in the art will realize that a large number of different parameters can be used, as an alternative to R-R interval comparisons, in order to verify correspondence between intracardiac data and external cardiac data.

DESCRIPTION OF THE PREFERRED EMBODIMENTS

Figure 1:
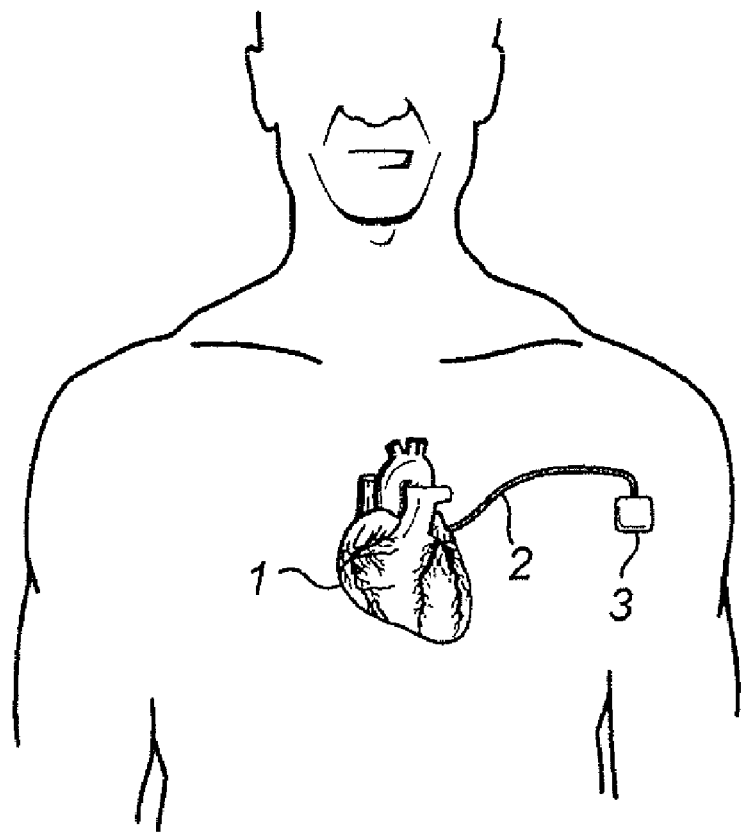
FIG. 1 is a schematic view of a patient's body showing a pacemaker implanted in the body.

FIG. 1 illustrates an implantable medical device (IMD) in the form of a pacemaker 3 implanted in a patient's body. A lead 2 connects the pacemaker 3 to the heart 1, thereby allowing stimulation of the heart 1 and control of the heart rhythm. In order to transmit and receive RF signals, the pacemaker 3 comprises a transceiver and an antenna.

Figure 2:
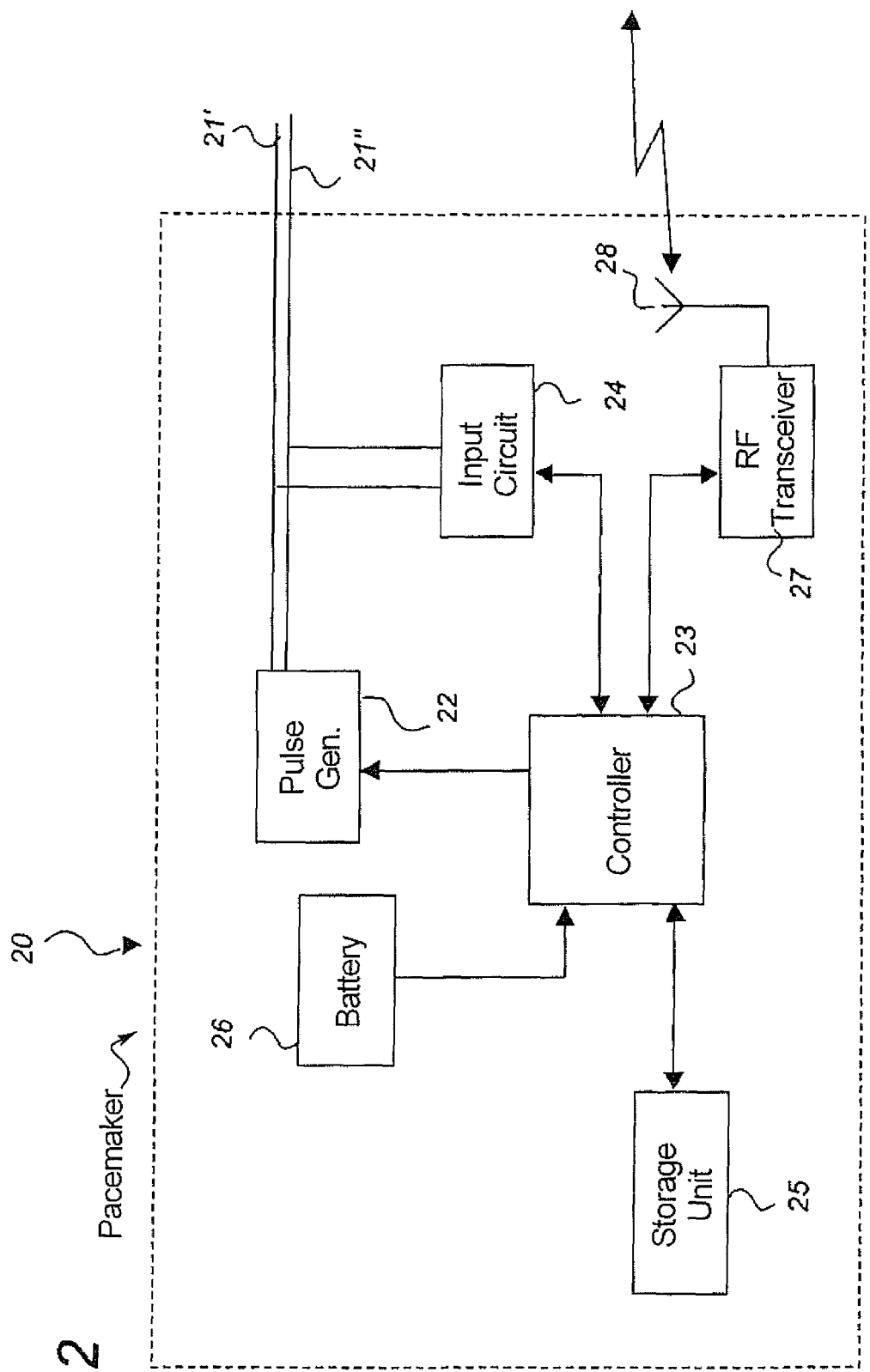
FIG. 2 illustrates functional blocks of an IMD in the form of a pacemaker, to which the present invention may be applied.

FIG. 2 illustrates functional blocks of a pacemaker 20 (in this particular case a bi-ventricular pacemaker) in more detail. The pacemaker 20 has a housing (not shown) that is hermetically sealed and biologically inert. Typically, the housing is conductive and may thus serve as an electrode. The pacemaker 20 is connectable to one or more pacemaker leads, where only two are shown in FIG. 2; namely a ventricular lead 21' implanted in the right ventricle of the heart and an atrial lead 21" implanted in the right atrium of the heart. The leads 21', 21" comprise one or more electrodes, such as a tip electrode or a ring electrode, arranged to, inter alia, measure impedance or transmit pacing pulses for causing depolarization of cardiac tissue adjacent to the electrodes generated by a pace pulse generator 22 under influence of a controller or controlling circuit 23 including a microprocessor for e.g. signal processing. The controller 23 controls, inter alia, pace pulse parameters such as output voltage and pulse duration.

Further, a storage unit 25 is connected to the controller 23, which storage unit 25 may include a random access memory (RAM) and/or a non-volatile memory such as a read-only memory (ROM). Detected signals from the patient's heart are processed in an input circuit 24 and are forwarded to the controller 23 for use in logic timing determination in known manner. The pacemaker 20 is powered by a battery 26, which supplies electrical power to all active electrical components of the pacemaker. The pacemaker 20 also comprises an RF transceiver 27 for wireless communication of signals to/from an external programmer. Medical personnel may e.g. want to monitor and/or adjust parameters of the pacemaker 20 of to perform reprogramming. The transceiver is connected to an antenna 28 via which the wireless communication occurs. The pacemaker 20 is typically arranged such that it can register an IEGM and provide it to an external programmer via the RF transceiver 27.

Figure 3:
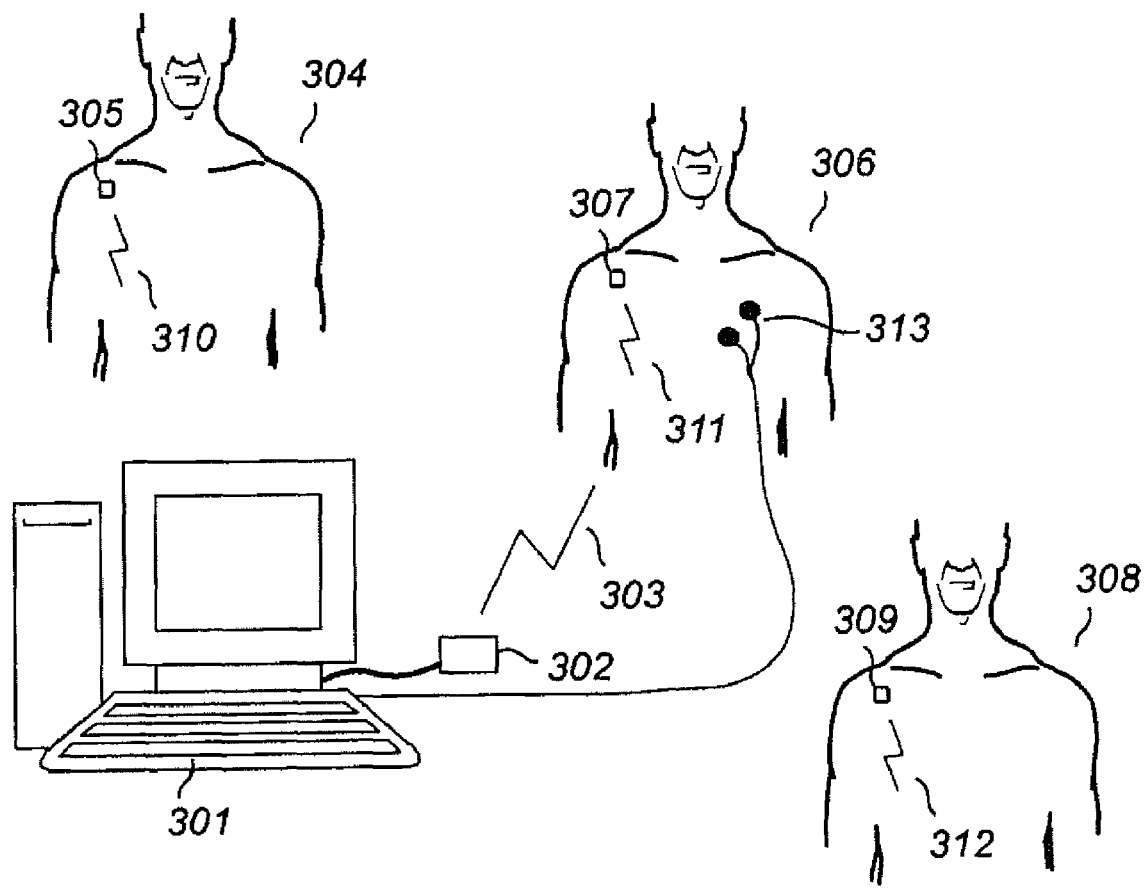
FIG. 3 shows an IMD telemetry device in accordance with an embodiment of the invention.

An IMD telemetry device in accordance with an embodiment of the invention is shown in FIG. 3. A programmer device 301 is employed to communicate with transceiver circuitry in IMDs. In principle, a programmer is a computer arranged with an RF transceiver 302 connected to the computer via an appropriate connection such as USB, a user interface for controlling the programmer and dedicated software designed for the purpose of communicating with an IMD. Even though not shown in FIG. 3, the RF transceiver may be arranged to conduct wireless transmissions with the programmer device. When establishing communication with an IMD, the programmer broadcasts a wake-up signal 303, i.e. a communication-initiating signal, before a communication session can be undertaken and IMDs within communication range of the programmer will respond to the wake-up signal. In this particular example, three patients 304, 306, 308 having a respective pacemaker 305, 307, 309 replies to the wake-up signal by means of transmitting a respective response signal 310, 311, 312 each comprising an identifier for the pacemaker in question. This identifier typically comprises the serial number of the IMD with which it is associated. In the prior art, when receiving the responses at the programmer, an operator of the programmer needs to determine from which one of the patients a particular response signal originates, which may be a cumbersome process. As has been previously mentioned in connection to discussing prior art, it is necessary for the operator of the external programmer to either directly observe a response-provoking event when the patient is in sight, or assist the patient in timing the response-provoking event when the patient is not in sight but is at least in voice communication with the operator.

The IMD telemetry system in accordance with an embodiment of the invention illustrated in FIG. 3 further comprises means for obtaining cardiac data obtained from a point on the body of a patient. In this particular exemplifying embodiment, the obtaining means are implemented in the form of electrodes 313 for recording an electrocardiogram (ECG) to be provided to the external programmer 301. The external programmer (and thus the operator of the programmer) may be located remotely from the patient 306, for example in another room. It is also possible that signals to be processed by the external programmer are transmitted to the programmer via a network. Now, when receiving responses 310, 311, 312 to the communication-initiating signal 303 transmitted from the programmer to the respective pacemaker 305, 307, 309, the pacemakers include intracardiac data, for example IEGM data in the respective response.

When receiving the IEGM data of the respective response, the respective set of IEGM data is compared to the recorded ECG data. Selected characteristics of the IEGM data is thus compared to corresponding characteristics of the ECG data, and when there is a match, the programmer device knows which one of the responses that originates from the patient to which the electrodes 313 are attached. Hence, the programmer can use the IMD identifier associated with the IEGM for which there is a match to initiate a communication session with the IMD 307 of the patient 306.

In the exemplifying embodiment shown in FIG. 3, a number of IMDs 305, 307, 309 respond to the communication-initiating signal. However, as should be understood from the above description, the present invention is also advantageous if a single IMD should respond to the communication-initiating signal. The operation of comparing features of an IEGM with corresponding features of an ECG (or some other appropriate cardiac data) ensures an operator of the external programmer that the received response actually originates from the patient to which the ECG sensors are attached.

The programmer device and its RF transceiver shown throughout the drawings typically employs the 402-405 MHz medical implant communication service (MICS) band for bidirectional communication with the IMDs. The MICS standard allows 10 channels, each 300 kHz, to be used in the 402-405 MHz band. Maximum output power is restrained to 25 μW. The IMDs should constantly be enabled, and for the communication-initiating signal (i.e. the wake-up signal), the 2.45 GHz industrial, scientific, and medical (ISM) band is used since less energy is required to power a receiver in this band.

Even though the invention has been described with reference to specific exemplifying embodiments thereof, many different alterations, modifications and the like will become apparent for those skilled in the art. The described embodiments are therefore not intended to limit the scope of the invention, as defined by the appended claims.

We claim as our invention:

1. A method of identifying an implantable medical device, which is arranged to be disposed in a body, for conducting a telemetry communication session between the implantable medical device and an external programmer device, the method comprising the steps of:
   transmitting a communication-initiating telemetry signal from said programmer device;
   receiving a telemetry response at the programmer device from at least one implantable medical device, said response comprising identification information identifying said at least one implantable medical device and intracardiac data derived from a patient in which said at least one implantable medical device is arranged to be disposed;
   receiving cardiac data obtained from a point on the body of a patient in which an implantable medical device is arranged to be disposed and with which the communication session is to be conducted; and
   comparing the cardiac data obtained from a point on the body of a patient with the intracardiac data, wherein the device with which the communication session is to be established is identified by means of said identification information if there is correspondence between the cardiac data obtained from a point on the body and the intracardiac data.

2. The method of claim 1, further comprising the step of:
   establishing, at the external programmer device, a communication session with the implantable medical device designated by the identification information.

3. The method of claim 1, wherein said cardiac data obtained from a point on the body of a patient comprises an electrocardiogram and said intracardiac data comprises an intracardiac electrogram.

4. The method of claim 3, wherein the comparison for correspondence between the surface electrocardiogram data and the intracardiac electrocardiogram data is based on PQRST cycles of the respective electrocardiogram data.

5. The method of claim 1, wherein the cardiac data obtained from a point on the body of a patient is received on a wireless channel.

6. The method of claim 1, wherein the cardiac data obtained from a point on the body of a patient is received via a wired connection.

7. The method of claim 1, wherein the step of comparing further comprises, if more than one response is received at the programmer device, comparing the cardiac data obtained from a point on the body of a patient with received sets of intracardiac data and identifying the device with which the communication session is to be established by means of using the identification information associated with the set of intracardiac data for which there is correspondence with said cardiac data obtained from a point on the body of a patient.

8. The method of claim 1, wherein the implantable medical device is a pacemaker.

9. A device for identifying an implantable medical device with which a telemetry communication session is to be conducted, the device comprising:
- a radio frequency transceiver; and
- processing circuitry configured to derive cardiac data obtained from a point on the body of a patient in which an implantable medical device is arranged to be disposed and with which the communication session is to be conducted;
- the transceiver being configured to transmit a communication-initiating telemetry, and to receive a telemetry response from at least one implantable medical device, said response comprising identification information identifying said at least one implantable medical device and intracardiac data derived from a patient in which said at least one implantable medical device is arranged to be disposed; and
- a comparator that compares the cardiac data obtained from a point on the body of a patient with the intracardiac data, the device with which the communication session is to be established being identified by said identification information if there is correspondence between the cardiac data obtained from a point on the body and the intracardiac data.

10. The device of claim 9, wherein said cardiac data obtained from a point on the body of a patient comprises an electrocardiogram and said intracardiac data comprises an intracardiac electrogram.

11. The device of claim 9, wherein said radio frequency transceiver is arranged to wirelessly receive said cardiac data obtained from a point on the body of a patient from the deriving means.

12. The device of claim 9, wherein said radio frequency transceiver is arranged to receive said cardiac data obtained from a point on the body of a patient from the deriving means via a wired connection.

13. The method of claim 1 further configured to compare, if more than one response is received, said cardiac data obtained from a point on the body of a patient with received sets of intracardiac data and identify the implantable medical device with which the communication session is to be established by using the identification information associated with the set of intracardiac data for which there is correspondence.

* * * * *